(12) United States Patent
Miller

(10) Patent No.: US 6,436,145 B1
(45) Date of Patent: Aug. 20, 2002

(54) PLUG FOR A MODULAR ORTHOPAEDIC IMPLANT AND METHOD FOR ASSEMBLY

(75) Inventor: Clayton Miller, Bremen, IN (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 09/586,079

(22) Filed: Jun. 2, 2000

(51) Int. Cl.[7] ................................................. A61F 2/38
(52) U.S. Cl. ................................. 623/20.34; 623/20.15
(58) Field of Search .......................... 623/20.14, 22.34, 623/20.15, 20.34; 403/67

(56) References Cited

U.S. PATENT DOCUMENTS

| | | | | |
|---|---|---|---|---|
| 4,936,853 A | * | 6/1990 | Fabian et al. ................. 623/20 |
| 5,405,403 A | * | 4/1995 | Mikhail ......................... 623/22 |
| 5,766,260 A | * | 6/1998 | Whiteside ...................... 623/22 |
| 6,099,569 A | * | 8/2000 | Keller ....................... 623/20.15 |
| 6,132,469 A | * | 10/2000 | Schroeder ................ 623/22.24 |

* cited by examiner

Primary Examiner—Bruce Snow
(74) Attorney, Agent, or Firm—Jacque R. Wilson

(57) ABSTRACT

An orthopaedic device for implanting on a bone includes a first component having a socket forming a first member of a morse taper lock. A second component has an end forming a second member of a morse taper lock received in the socket. A protuberance is provided on one of the first and second members. Impacting the second component inserted in the socket seats the second component in the socket, and creates a localized deformation of the interference fit between the first and second components and establishes a barrier to the passage of debris.

2 Claims, 4 Drawing Sheets

PLUG FOR A MODULAR ORTHOPAEDIC IMPLANT AND METHOD FOR ASSEMBLY

BACKGROUND OF THE INVENTION

1. Field of the Invention

The present invention relates to orthopaedic implants, and, more particularly, to a modular orthopaedic implant having a taper lock joint, and to methods for assembling such modular orthopaedic components.

2. Description of the Related Art

Orthopaedic implants used to reconstruct a joint of a patient typically include two implant halves, with each implant half defining an articulating bearing surface. For example, an orthopaedic knee implant includes a femoral knee component which is placed within the distal femur and a tibial component which is placed within the proximal tibia. The femoral knee component typically includes a metallic articulating bearing surface which pivots on a non-metallic articulating bearing surface defined by the tibial knee component. The non-metallic bearing surface may be formed from a block of ultra-high molecular weight polyethylene (UHMWPE) which is machine to define the articulating bearing surface. The non-metallic bearing surface is attached to and carried by a tibial tray. The tray may in turn be affixed to a stem inserted within the intramedullary canal of the tibia. Pivotal movement between the femoral component and the bearing surface of the tibial component occurs with relatively low friction and wear characteristics.

To accommodate anatomical variations and differing surgical needs, it is known to provide a modular structure for the tibial component, which allows the assembly of different combinations of the bearing, tibial tray and tibial stem to meet the needs presented by the patient conditions. In one such modular structure, the tibial stem for the tibial knee component has a frustum shaped outer surface, and a complimentary tapered receiving member or socket on the tibial tray provides an interference fit in the nature of a morse taper lock between the tibial tray and the tibial stem, for affixing the tibial tray to the tibial stem. It is also known to provide a plug as an alternative to a stem where filling of the receiving member is desirable without an extending stem. Instances where such a plug is desirable include filling the receiving member to prevent debris transmission and providing a threaded plug for receiving an attachment screw to facilitate modular implant assembly.

SUMMARY OF THE INVENTION

The present invention provides an orthopaedic device having a first component and a second component having a novel structure providing affixation between components, and which further provides a barrier to contamination flow between the intramedullary canal and the articulating bearing surfaces.

The invention comprises, in one form thereof, an orthopaedic device having a first orthopaedic component including a first end defining an articulating bearing surface and a second end defining a first member of a morse taper lock; and a second orthopaedic component including a first end defining a second member of the morse taper lock. One of the first member and the second member includes a surface having a protuberance thereon.

The invention comprises, in another form thereof, an orthopaedic knee component for implanting within a proximal tibial. A tibial tray includes a proximal tibial plateau and a distally extending socket having an internal surface and defining a female member of a morse taper lock. A tibial plug has a proximal end having a tapered outer surface and defining a male member of the morse taper lock. A protuberance on the outer surface of the tibial plug creates localized deformation when the morse taper lock is assembled.

The invention comprises, in still another form thereof, a method for assembling a modular orthopaedic device. Steps of the method include providing a first component with a female member of a morse taper; providing a second component with a male member of the morse taper lock having a surface thereof with a protuberance thereon; engaging the male member of the morse taper lock with the female member of the morse taper lock; and impacting the second component, seating the second component in the first component and permanently deforming at least one of the protuberance, the female member and the male member.

An advantage of the present invention is that a known taper lock of a modular orthopaedic implant is provided with locking security between the components of the taper lock.

Another advantage of the present invention is that a barrier is formed to inhibit the passage of material between the distal end and the proximal end of a modular tibial implant.

BRIEF DESCRIPTION OF THE DRAWINGS

The above-mentioned and other features and advantages of this invention, and the manner of attaining them, will become more apparent and the invention will be better understood by reference to the following description of several embodiments of the invention taken in conjunction with the accompanying drawings, wherein.

Figure 1:
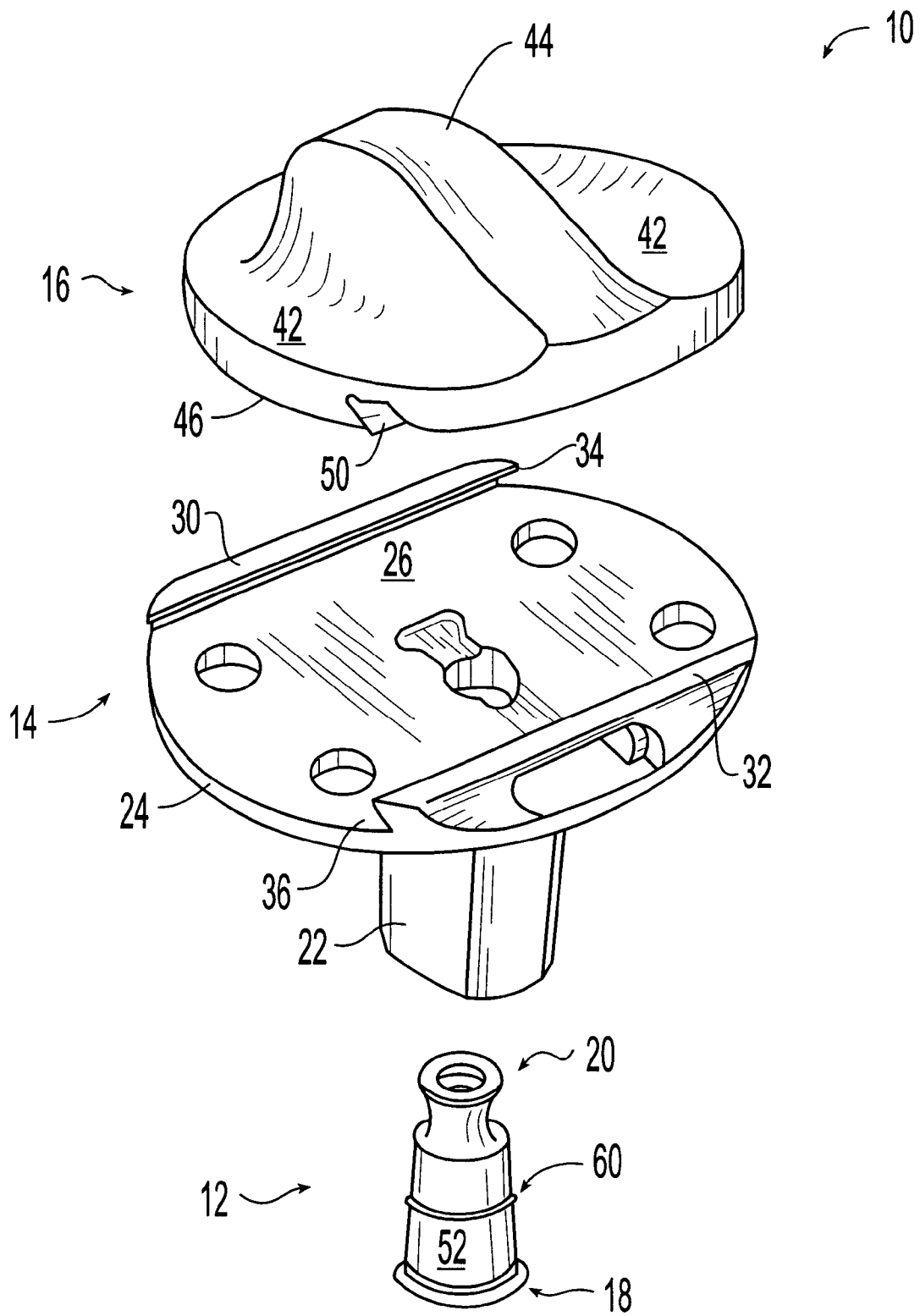
FIG. 1 is an exploded perspective view of a tibial knee component of the present invention.

Corresponding reference characters indicate corresponding parts throughout the several views. The exemplifications set out herein illustrate a preferred embodiment of the invention, in several variations, and such exemplifications are not to be construed as limiting the scope of the invention in any manner.

DETAILED DESCRIPTION OF THE INVENTION

Referring now to the drawings, and more particularly to FIG. 1, there is shown an exemplary orthopaedic device in the form of a tibial knee component 10 designed to be implanted within a proximal tibia (not shown). Tibial knee component 10 engages with a femoral knee component (not shown) which is implanted within a distal femur, as those knowledgeable in the art will understand readily.

Tibial knee component 10 is modular in design, and includes a tibial plug 12, a tibial tray 14 and a bearing 16, each of which may be provided in different sizes and varying configurations, and combined as needed. A proximal end 20 of tibial plug 12 is adapted for engagement with and attachment to tibial tray 14. Tibial tray 14 has a distally extending socket 22 adapted for engagement with and attachment to proximal end 20 of tibial plug 12, as will be described more fully hereinafter. Tibial tray 14 further includes a proximal tibial plateau 24 having a generally planar proximal surface 26 which extends transverse (e.g., generally orthogonal) to a longitudinal axis of socket 22.

Tibial tray 14 also includes a first retaining wall 30 and a second retaining wall 32, each including an undercut 34, 36, respectively. Undercut 34 of first retaining wall 30 extends the full length of first retaining wall 30, and undercut 36 of second retaining wall 32 extends the full length of second retaining wall 32. First and second retaining walls 30 and 32 are disposed near outer edges of tibial plateau 24, essentially on opposite sides of tibial plateau 24, and together with design features of bearing 16 to be described hereinafter, secure bearing 16 to tibial tray 14.

Bearing 16 has an articular bearing surface 42 for engagement with the femoral component. Articular bearing surface 42 is disposed on either side of a center projection 44. Each discrete portion of articular bearing surface 42 on either side of projection 44 engages a corresponding condyle (not shown) of the femoral knee component, with center projection 44 being disposed between the condyles.

Figure 2:
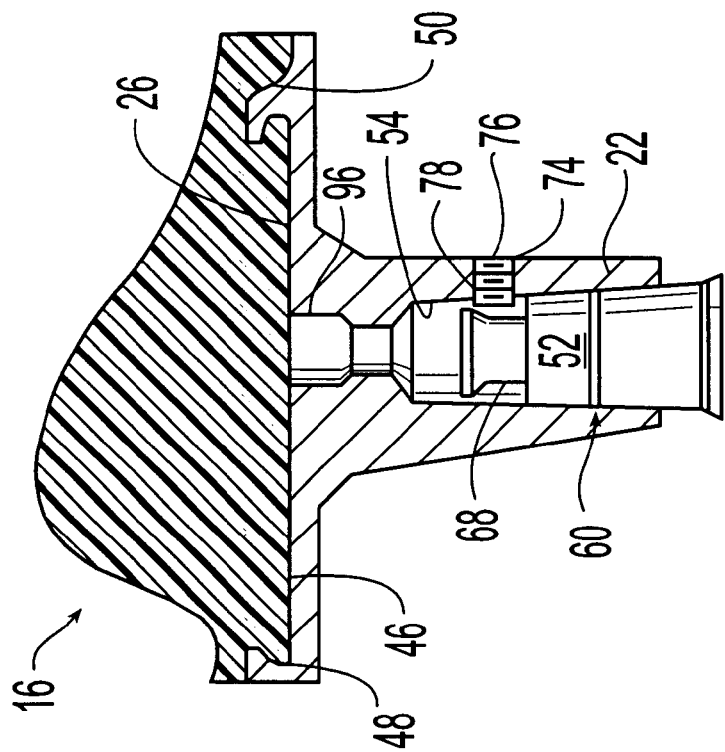
FIG. 2 is a cross-sectional view of an assembled tibial knee component of the present invention, showing also a modification to the embodiment shown in FIG. 1.

Bearing 16 has a backing surface 46 which engages with tibial plateau 24. Backing surface 46 is generally planar, and shaped to match the corresponding generally planar configuration of proximal surface 26 of tibial plateau 24. Backing surface 46 defines a load bearing surface with tibial plateau 24, which transfers the load imparted either by tibial plateau 24 or the femoral condyles engaging articular bearing surface 42. As illustrated in FIG. 2, backing surface 46 of bearing 16 is sized and configured such that backing surface 46 is substantially entirely supported by tibial plateau 24, and includes a first channel 48 and a second channel 50 adapted and arranged to engage first retaining wall 30 and second retaining wall 32, respectively. Bearing 16 is assembled onto tibial tray 14 by engaging first channel 48 with first retaining wall 30, and engaging second channel 50 with second retaining wall 32. Engagement may be achieved by aligning channels 48 and 50 with retaining walls 30 and 32, at ends thereof, and sliding bearing 16 on to tibial tray 14. In the embodiment shown, bearing 16 is constructed from a plastic (e.g., UHMWPE) and tibial tray 14 is constructed from a metal (e.g., cobaltchromium alloy).

It is known to provide proximal end 20 of tibial plug 12 in a conical or frustoconical shape, having a tapered outer surface 52; and to provide socket 22 in an appropriate size and shape to receive proximal end 20 therein. An internal surface 54 in socket 22 is of an appropriate shape and taper with respect to the shape and taper of outer surface 52 such as to provide an interference fit between internal surface 54 and outer surface 52 when proximal end is inserted deeply into socket 22. Thus, socket 22 is the female member, and proximal end 20 is the male member of a so-called morse taper lock. Outer surface 52 and internal surface 54 are engagement surfaces of the taper lock, for securing the tibial tray 14 to tibial plug 12.

Figure 6:
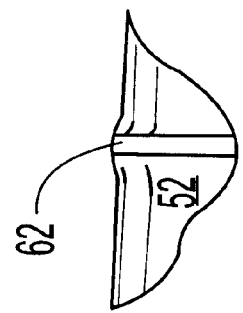
FIG. 6 is an enlarged perspective view of the area designated by numeral 6 in FIG. 4.
Figure 4:
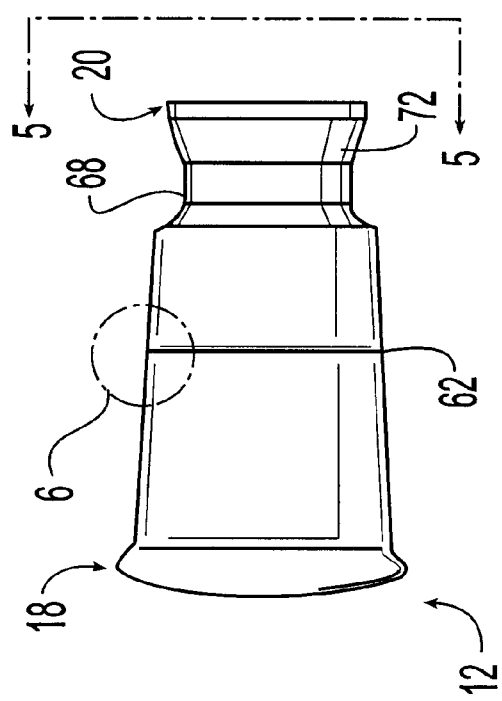
FIG. 4 is an enlarged perspective view of the tibial plug shown in the preceding Figs.
Figure 8:
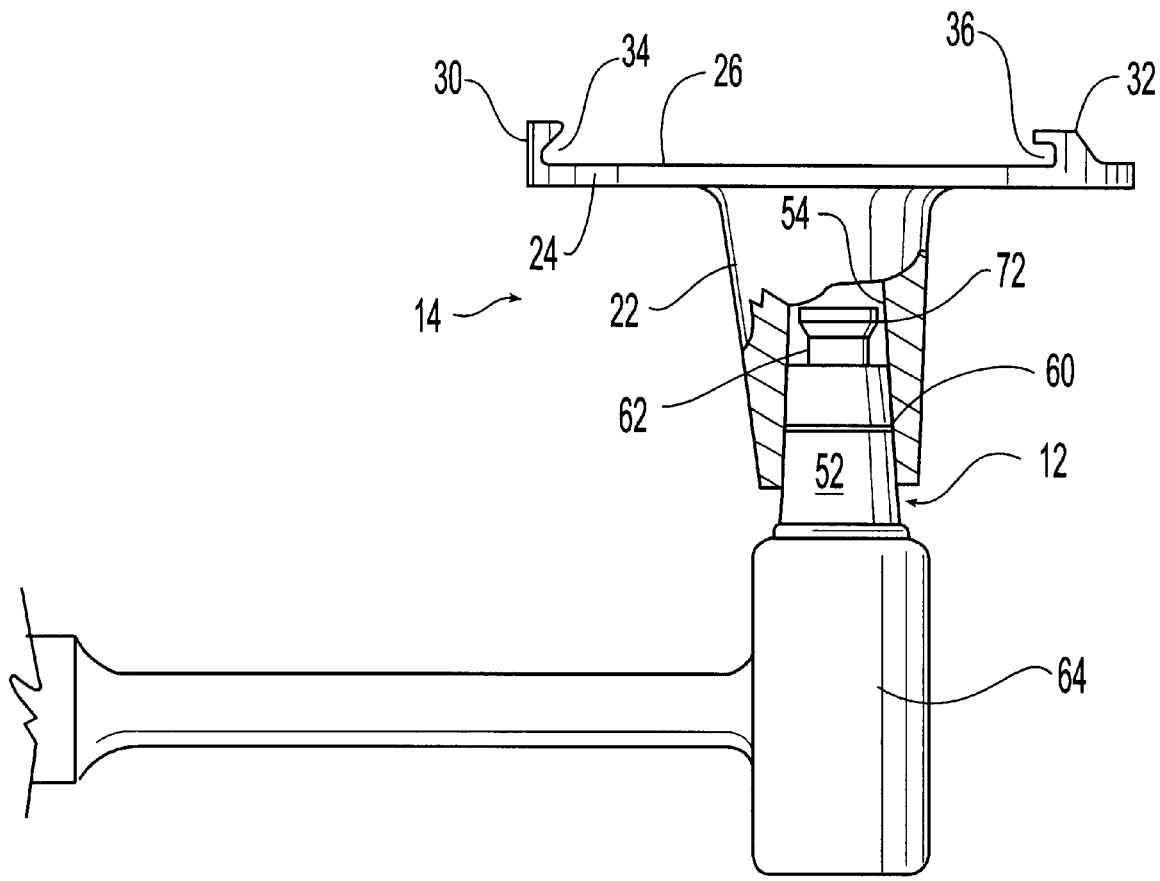
FIG. 8 is a perspective view, in partial cross-section, illustrating the manner of assembling the tibial plug and the tibial tray of the present invention.

In accordance with an aspect of the present invention, a protuberance 60 is provided on outer surface 52 of proximal end 20, to provide interference and thereby securement between internal surface 54 and outer surface 52. As can been seen most clearly in the enlarged views of FIG. 4 and FIG. 6, protuberance 60 may take the form of a ridge 62 circumferentially disposed in outer surface 52, formed during machining of surface 52. As proximal end 20 of tibial plug 12 is forced deeply into socket 22, such as by impacting with a mallet 64 (FIG. 8), localized deformation occurs along ridge 62, creating an intimate contact between the outer surface 52 and internal surface 54 in the area of the deformation. Depending on the hardness of materials used to form the components, the deformation may occur to protuberance 60, outer surface 52 and/or internal surface 54.

Figure 7:
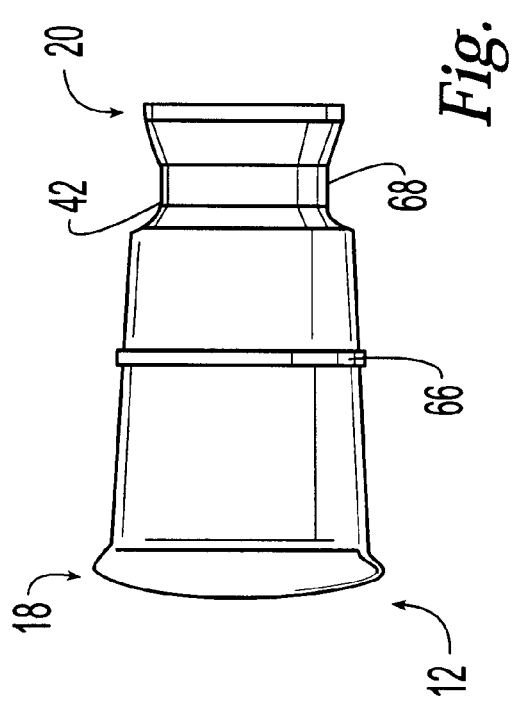
FIG. 7 is a perspective view of yet another modified form of the tibial knee component of the present invention.

As shown in FIG. 7, protuberance 60 also may take the form of an o-ring 66 disposed about outer surface 52 of tibial plug 12 proximal end 20. O-ring 66 may be made of suitable metal, plastic, rubber or elastomeric material. A groove, not shown, may be provided in outer surface 52 to receive and retain o-ring 66. Similarly to the previous description for ridge 62, as proximal end 20 is forced deeply into socket 22, localized deformation occurs along o-ring 66.

In accordance with another aspect of the present invention, outer surface 52 of proximal end 20 further may include a circumferential recessed area 68, which is recessed from outer surface 52 and defines a proximal abutment 72. A threaded opening 74 (FIG. 2) in socket 22 is aligned with recessed area 68 when tibial plug 12 is fully inserted in socket 22. Threaded opening 74 receives a correspondingly threaded set screw 76, an inner tip 78 of which is seated in recessed area 68, when set screw 76 is advanced sufficiently through threaded opening 74. When seated in recessed area 68, set screw 76 further secures the axial position of tibial plug 12 within socket 22, as relative axial movement between tibial plug 12 and socket 22 is constrained by the interference of set screw 76 inner tip 78 with proximal abutment 72. It should be understood that set screw 76 is one type of suitable locking member, which may also include other keys and the like forming an attachment between tibial plug 12 and socket 22. For example, inner tip 78 also could be received in a threaded opening in distal end 18 of tibial plug 12.

Figure 3:
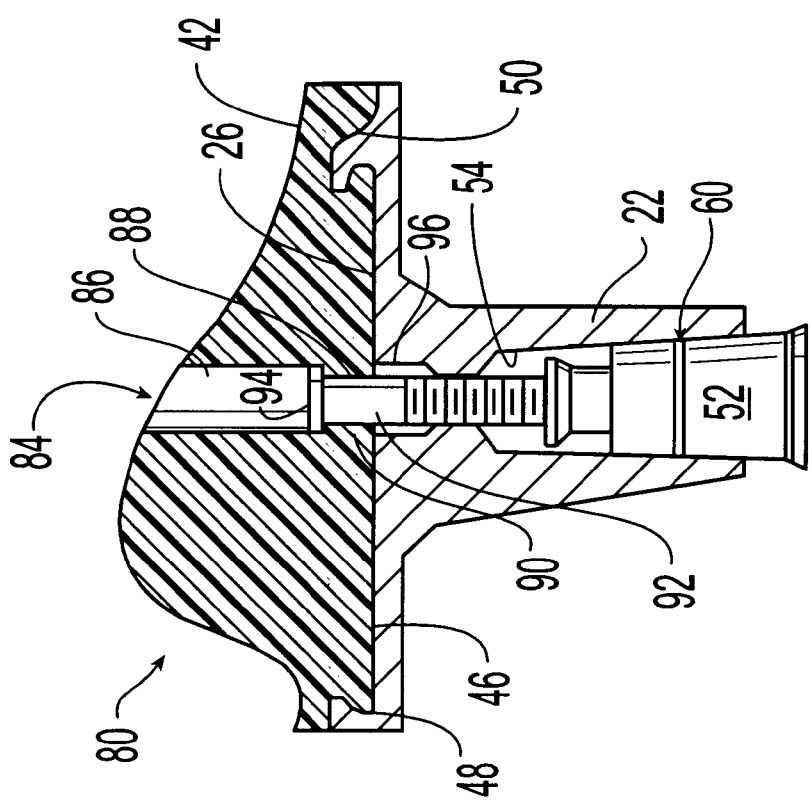
FIG. 3 is a cross-sectional view similar to that of FIG. 2, but showing the structure for the attachment of a bearing different from that shown in FIG. 1 and FIG. 2.
Figure 5:
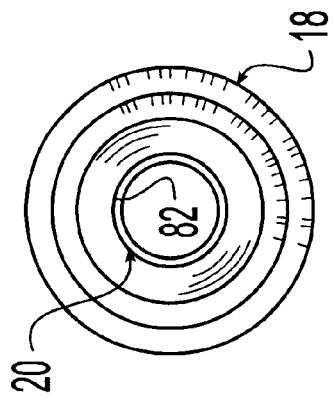
FIG. 5 is an end view of the tibial plug shown in FIG. 4, the view taken in the direction 5—5 shown in FIG. 4.

Under some conditions, a thicker bearing 80, (FIG. 3), may be used. Enhanced fixation may be obtained where proximal end 20 of tibial plug 12 is provided with an internally threaded bore 82, shown in FIG. 5. Bearing 80 includes a hole 84 extending therethrough, from the top thereof to backing surface 46. The diameter of an upper portion 86 of hole 84 nearer articular bearing surface 42 is greater than the diameter of a lower portion 88 of hole 84 nearer backing surface 46. At the transition between upper portion 86 and lower portion 88, a shoulder 90 is defined. A threaded bolt 92, having a head 94, may be inserted partially through hole 84. Bolt 92 may be advanced through upper portion 86, with head 94 being of a size to pass through upper portion 86, but not through lower portion 88. A hole 96 in tibial tray 14 extends from proximal surface 26 to socket 22, and is aligned with hole 84 of bearing 80. Bolt 92 extends through hole 96 so that threads of bolt 92 engage threaded bore 82 in plug 12. Bolt 92 is advanced within threaded bore 82 until head 94 of bolt 92 is seated against shoulder 90, securing backing surface 46 of bearing 80 to tibial plateau 24. Properly secured, head 94 of bolt 92 is disposed in hole 84 well below articular bearing surface 42 of bearing 80.

In the use of a tibial knee component 10 of the present invention, after having determined the appropriate size and type of tibial plug 12, tibial tray 14 and bearing 16, 80 to be used, tibial plug 12 is affixed to tibial tray 14 by placing proximal end 20 of tibial plug 12 in socket 22 of tibial tray 14. Proximal end 20 is inserted deeply into socket 22, and is set securely in place such as by applying an impact to distal end 18 by striking with mallet 64 or the like. Deformation of or around protuberance 60 results. Deformation may occur in outer surface 52, in internal surface 54, and/or to protuberance 60, depending on the physical characteristics of the material used for each. For embodiments provided with the feature, set screw 76 is advanced inwardly, to set inner tip 78 thereof against proximal abutment 72. Bearing 16, 80 is attached to tibial tray 14, as described previously, and in the use of a bearing such as bearing 80, head 94 of bolt 92 is tightened against shoulder 90.

In addition to the securement of tibial plug 12 in socket 22 of tibial tray 14, the intimate engagement of protuberance 60 and internal surface 54 and the deformation which occurs to protuberance 60 or around and along protuberance 60 in outer surface 52 or internal surface 54, create a barrier to the passage of materials along the region defined between outer surface 52 and internal surface 54. The barrier, for example, inhibits passage of debris between the intramedullary canal and the articulating bearing surfaces. Contaminants are thereby inhibited from flowing in either direction through the morse taper lock.

It should be understood that the concepts of the present invention can be used with other types of orthopaedic devices having taper lock joint, e.g., hip implants, shoulder implants, and others with taper lock joints. Likewise, variations to the exemplary embodiment described herein may be made. Different sizes, shapes and configurations of tibial plugs, tibial trays and bearings may be combined, as necessary, for the conditions presented. Variations in construction may be used. For example, while tibial tray 14 has been shown and described having socket 22 defining a female member of the taper lock, and tibial plug 12 defining the male member of the taper lock, a socket such as socket 22 can be provided on tibial plug 12, and a corresponding male member of the taper lock defined by the distal end of tibial tray 14.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopaedic knee component for implanting within a proximal tibia, comprising:

a tibial tray including-a proximal tibial plateau and a distally extending socket having an internal surface and defining a female member of a morse taper lock;

a bearing carried by said tibial tray on said proximal tibial plateau, and having an articular bearing surface for engagement with a femoral component; and a tibial plug having a proximal end and a distal end, said proximal end of said tibial plug having a tapered outer surface and defining a male member of said morse taper lock, said tapered outer surface having a protuberance thereon, wherein said protuberance comprises a circumferential ridge in said outer surface of said tibial plug, and wherein each said ridge and said internal surface of said socket are intimately engaged and define localized deformation such that said ridge and said localized deformation define a means for inhibiting contaminant flow through said morse taper lock and said socket defines a threaded opening therethrough; and a set screw disposed in threaded engagement with said threaded opening and extending from said socket to said tibial plug, wherein a recessed area in said outer surface defines a proximal abutment surface and said set screw includes an inner tip received by said proximal abutment surface.

2. An orthopaedic knee component for implanting within a proximal tibia, comprising:

a tibial tray including a proximal tibial plateau and a distally extending socket having an internal surface and defining a female member of a morse taper lock;

a bearing carried by said tibial tray on said proximal tibial plateau, and having an articular bearing surface for engagement with a femoral component; and a tibial plug having a proximal end and a distal end, said proximal end of said tibial plug having a tapered outer surface and defining a male member of said morse taper lock, said tapered outer surface having a protuberance thereon, wherein said protuberance comprises a circumferential ridge in said outer surface of said tibial plug, and wherein each said ridge and said internal surface of said socket are intimately engaged and define localized deformation such that said ridge and said localized deformation define a means for inhibiting contaminant flow through said morse taper lock and said socket defines a threaded opening therethrough; and a set screw disposed in threaded engagement with said threaded opening and extending from said socket to said tibial plug, wherein said proximal end of said tibial plug defines a thread bore, and a bolt extending through said bearing and said tibial tray is engaged with said threaded bore.

* * * * *